(12) United States Patent
Vega Carrasco et al.

(10) Patent No.: US 8,455,452 B2
(45) Date of Patent: Jun. 4, 2013

(54) COMPOSITION AND USE OF A LONG-ACTING ORAL BIOADHESIVE ENDOPARASITICIDE GEL BASED ON DORAMECTIN

(75) Inventors: Edgar Régulo Vega Carrasco, Lima (PE); José Fernando Tang Ploog, Lima (PE); Jorge Fabián Ruiz Herrera, Lima (PE); Umberto Calderon Ojeda, Lima (PE)

(73) Assignee: Agrovet Market, S.A., Lima (PE)

( * ) Notice: Subject to any disclaimer, the term of this patent is extended or adjusted under 35 U.S.C. 154(b) by 71 days.

(21) Appl. No.: 13/062,419

(22) PCT Filed: Aug. 28, 2009

(86) PCT No.: PCT/IB2009/006867
§ 371 (c)(1), (2), (4) Date: Mar. 4, 2011

(87) PCT Pub. No.: WO2010/032113
PCT Pub. Date: Mar. 25, 2010

(65) Prior Publication Data
US 2011/0160155 A1  Jun. 30, 2011

(30) Foreign Application Priority Data
Sep. 19, 2008  (PE) .............................. 001551-2008

(51) Int. Cl.
*A61K 31/70* (2006.01)
(52) U.S. Cl.
USPC .......................................................... 514/30
(58) Field of Classification Search
USPC .......................................................... 514/30
See application file for complete search history.

(56) References Cited

U.S. PATENT DOCUMENTS

| 5,756,474 A | * | 5/1998 | Furstenau | 514/30 |
| 6,893,652 B2 | * | 5/2005 | Sabnis et al. | 424/407 |

* cited by examiner

*Primary Examiner* — Elli Peselev
(74) *Attorney, Agent, or Firm* — McNeely, Hare & War LLP; Simana Rao, Esq.; William Hare, Esq.

(57) ABSTRACT

The present invention relates to a bioadhesive endoparasiticidal gel composition comprising doramectin, having a high degree of adhesion to equine oral mucosa and having a sweet flavor greatly facilitating the dosing thereof, methods for the preparation thereof and methods for treating a condition comprising administering said composition.

26 Claims, No Drawings

COMPOSITION AND USE OF A LONG-ACTING ORAL BIOADHESIVE ENDOPARASITICIDE GEL BASED ON DORAMECTIN

CROSS-REFERENCE TO RELATED APPLICATIONS

This application claims priority to PCT International Application No. PCT/IB2009/006867 filed on Aug. 28, 2009, which claims priority from Peruvian Patent Application No. 001551-2008, filed Sep. 19, 2008, said applications being wholly incorporated herein by reference.

BACKGROUND

Gastrointestinal helminthosis is a parasitic condition caused by nematodes of diverse families, such as the Strongylus type family. Parasitosis of this type causes serious gastrointestinal disorders which negatively and constantly affect the production and productivity of equine livestock.

For this reason, effective control of gastrointestinal helminthosis is of great importance and advantageously achievable through the use of suitable antihelmintic agents such as doramectin.

Doramectin (25-cyclohexyl-5-O-dimethyl-25-de(1-methylpropyl)avermectin $A_1$) is a biosynthetic drug derived from the fermentation of avermectin, from fermenting *Streptomyces avermitilis*, with an effect that is very similar to that of other avermectins in terms of spectrum and pharmacokinetics and absorption.

Doramectin is surprisingly a drug that has never before been used in the dosage form of an oral gel in equine livestock. In contrast, this chemical compound is administered to other species generally by parenteral administration, and infrequently by topical and oral administration due to limitations concerning the concentration of active ingredients together with the organoleptic and physicochemical characteristics of the compositions known up until the present.

U.S. Pat. No. 5,756,474 describes compositions of oral liquid solutions based on doramectin; however the compositions described by the mentioned patent do not include the dosage form of an oral gel. Additionally, the compositions described in the mentioned patent do not include within their physical characteristics adhesion to the oral cavity as an administration advantage which, in contrast, is considered in the present invention, together with the prolonged action of the drug and the palatability generated by the action of the sweetening agents.

U.S. Pat. No. 6,165,987 describes antihelmintic compositions based on the administration of drugs belonging to the avermectin and milbemycin groups, in combination with praziquantel; however the compositions described in the mentioned patent, like U.S. Pat. No. 5,756,474, do not consider the dosage form of a gel by relating only to injectable and oral liquid solutions. Additionally, the compositions described in the mentioned patent do not include within their physical characteristics adhesion to the oral cavity as an administration advantage which, in contrast, is considered in the present invention, together with the prolonged action of the drug and the palatability generated by the action of the sweetening agents.

U.S. Pat. No. 6,893,652 describes a combined endoparasiticidal gel composition; however the compositions described by the mentioned patent do not include within their physical characteristics adhesion to the oral cavity as an administration advantage which, in contrast, is considered in the present invention. Additionally, the compositions of the mentioned patent only include the combinations of moxidectin and praziquantel without considering doramectin.

SUMMARY

Gastrointestinal helminthosis is a parasitic condition caused by nematodes of diverse families causing serious gastrointestinal disorders in equine livestock. Control of this illness is of great importance and advantageously achievable through the use of suitable antihelmintic agents such as doramectin, which is a chemical compound widely administered by parenteral route and infrequently by oral route in liquid form due to the organoleptic and physicochemical characteristics of the compositions known up to the present. The present invention demonstrates that it is possible to administer doramectin in the dosage form of an oral gel at concentrations of up to 5.0% weight/volume, overcoming the organoleptic and physicochemical restrictions of the compositions known up to the present. Factors never heretofore included in oral endoparasiticidal compositions based on doramectin, presenting a wide differential advantage compared with the compositions known up to the present. These and other features, objectives and advantages of the present invention will be appreciated by the person skilled in the art from the detailed description provided below in the present document, as well as in the attached claims.

DETAILED DESCRIPTION

The present invention relates to a single-application, prolonged action bioadhesive endoparasiticidal gel composition based on doramectin having a high degree of adhesion to the oral mucosa of treated mammals and having a sweet flavor greatly facilitating the dosing thereof, to methods for the preparation thereof and to its use as an endoparasiticide in mammals, mainly equines.

The present invention advantageously demonstrates, unlike the aforementioned patents, that it is possible to administer doramectin in the dosage form of an oral gel, at concentrations of up to 5.0% weight/volume, being long-acting and also having a sweet favor and considerable adhesion to the oral cavity. Factors never heretofore included in oral endoparasiticidal compositions based on doramectin, presenting a wide differential advantage compared with the compositions known up to the present.

For that reason the objectives of the present invention are to provide one or more of:

An oral endoparasiticidal gel composition based on doramectin for equine livestock.

An oral endoparasiticidal gel composition based on doramectin which maintains the mentioned active ingredient in solution at concentrations of up to 5.00% weight/volume.

A long-acting oral endoparasiticidal gel composition based on doramectin which shows a proven effectiveness of up to 60 days after being administered.

An oral endoparasiticidal gel composition based on doramectin with a sweet flavor which enhances the voluntary ingestion thereof.

An oral endoparasiticidal gel composition with a high degree of adhesion to the mucosae of the oral cavity which reduces the probability of voluntary or involuntary expulsion thereof after being administered.

This composition of "oral bioadhesive endoparasiticidal gel" comprises:

a) from 0.50% to 5.00%; preferably from 1.00% to 4.00%; more preferably from 1.50% to 2.50% weight/volume of doramectin.
b) from 1.00% to 10.00%; preferably from 2.00% to 5.00%; more preferably from 2.50% to 3.50% weight/volume of an organic solvent such as N-methyl-2-pyrrolidone, 2-pyrrolidone, benzyl alcohol, glycerol formal, similar components or mixtures thereof.
c) From 10.00% to 60.00%; preferably from 20.00% to 50.00%; more preferably from 30.00% to 40.00% weight/volume of polyvinylpyrrolidone.
d) From 25.00% to 95.00% volume/volume of a diluent such as propylene glycol, polyethylene glycol 300, polyethylene glycol 400, glycerin, polyethoxylated castor oil, macrogol 15 hydroxystearate, similar components or mixtures thereof.
e) From 0.10% to 4.00%; preferably from 0.50% to 3.00%; more preferably from 1.00% to 2.50% of a sweetening agent such as sodium sucralose, sodium saccharin, sucrose, similar components or mixtures thereof
f) From 0.10% to 4.00%; preferably from 1.00% to 3.00%; more preferably from 1.50% to 2.50% weight/volume of a flavoring agent which is a natural or synthetic essence.
g) From 0.10% to 1.00%; more preferably from 0.18% to 0.22% weight/volume of a preservative such as methylparaben, propylparaben, butylparaben, similar components or mixtures thereof.
h) From 0.001% to 0.010%; more preferably from 0.0015% to 0.0025% weight/volume of a water-soluble azo dye, such as allura red dye, and similar components and mixtures thereof.

The effective amounts of the present invention can vary depending on the general state of health of the animal, the degree of infestation, the age of the animal and the infested organs. Generally, amounts of the present "long-acting oral bioadhesive endoparasiticidal gel" sufficient for providing amounts of 200 micrograms of doramectin per kilogram of body weight of the infested equine livestock are suitable.

The present invention also provides a method for the preparation of a "long-acting oral bioadhesive endoparasiticidal gel" composition comprising one or more of the following steps:

1. Mixing the doramectin, the preservative, the coloring agent and the organic solvent until forming solution "A".
2. Mixing the diluent with the sweetening agent until forming solution "B".
3. Mixing solution "B" with the polyvinylpyrrolidone until forming gel "C".
4. Mixing gel "C" with solution "A" until forming gel "D".
5. Mixing the flavoring agent with gel "D" until forming gel "E".
6. Mixing gel "E" in a vacuum to form an air-free endoparasiticidal gel composition.

Example 1

| Oral endoparasiticidal gel composition based on Doramectin | |
| --- | --- |
| doramectin | 2.000% w/v |
| sucralose | 1.000% w/v |
| 2-methylpyrrolidone | 3.000% w/v |
| Apple essence | 1.000% w/v |
| allura red dye | 0.002% w/v |
| methylparaben | 0.180% w/v |
| propylparaben | 0.020% w/v |
| polyvinylpyrrolidone | 40.000% w/v |
| polyethylene glycol 300 | QSF 100.000% v/v |

Method of Preparation

1. Mixing the doramectin, methylparaben, propylparaben, allura red dye and 2-methyl pyrrolidone until forming solution "A".
2. Mixing the polyethylene glycol 300 with the sucralose until forming solution "B".
3. Mixing solution "B" with the polyvinylpyrrolidone until forming gel "C".
4. Mixing gel "C" with solution "A" until forming gel "D".
5. Mixing the apple essence with gel "D" until forming gel "E".
6. Mixing gel "E" in a vacuum to form an air-free oral endoparasiticidal gel composition.

Example 2

Work Summary: Evaluation of the Efficacy of an Antiparasite Administered by Oral Route Containing Doramectin (doraQuest I.a®) for Control of Parasitosis in Equines Evaluation of the tolerance and effectiveness against nematodes of an oral endoparasiticidal gel composition based on doramectin at 2.00% weight/volume in naturally infected equines.

Study Site

The evaluation was performed in the Escuela de Equitación del Ejército (Riding School of the Army), located in the La Molina district in Lima, Peru, located at approximately 500 meters above sea level, with a temperate climate. The study was performed between the months of January to March 2007.

Animals

A total of 20 equines were incorporated in the study, comprising males and females of different ages, naturally infected with gastrointestinal parasites, and being selected by means of fecal studies using the Mc Master technique, the animals having figures above 200 eggs per gram of feces (epg), the "Strongylus" type eggs standing out, among others. The average age was five years (range: 3 to 9 years), with an average weight of 350 Kg.

To assign the animals to the work groups, they were listed in decreasing order according to the egg count per gram of feces to subsequently be equally distributed into each of the two experimental groups.

Experimental Groups

Control Group: 10 untreated equines

Treated Group: 10 equines treated with the oral endoparasiticidal gel composition of the present invention.

All the animals were kept under the same handling conditions and environmental effects throughout the evaluation period in the facilities of the Escuela de Equitación del Ejército del Peru (Riding School of the Peruvian Army).

Fecal Parasitological Analyses conducted

Throughout the study period, fecal samples of the selected animals were collected and identified, being analyzed by means of floating and Mc Master methods at 0, 7, 14, 21, 28, 35, 42, 49, 63 and 70 days after treatment.

Analysis of the Results

The percentage of efficacy was determined by means of the formula described by Powers et al. (1982), where:

$$\% \text{ efficacy} = \frac{\text{Arithmetic mean control group} - \text{Arithmetic mean treated group}}{\text{Arithmetic mean control group}} \times 100$$

The efficacy was evaluated according to the following criterion:

Highly effective >98%
Effective 90-98%
Aid in control 80-89%.
Insufficiently active <80% (not recordable)

The results were expressed in percentages of efficacy for the drug under evaluation. (MERCOSUR 1998)

Results

The first fecal parasitological evaluation provided an arithmetic average of 595 Strongylus type parasite eggs per gram of feces. These results are seen in Table 1.

All the positively diagnosed animals treated with the composition of the present invention responded to therapy showing a total reduction of the number of Strongylus type eggs present in feces from day 7 post-treatment up to day 63.

Conclusion

The results obtained in the present study determined that the oral endoparasiticidal gel of the present invention:

was highly effective against Strongylus type eggs in equine livestock up to day 66.
was effective against Strongylus type eggs in equine livestock up to day 70.
no local or systemic adverse reactions or abnormalities were observed in the health that could be attributed to treatment with the composition of the present invention in any of the treated animals.

TABLE 1

Arithmetic average of parasite eggs per gram of feces (epg) by means of the McMaster technique and efficacy percentage of the oral endoparasiticidal gel of the present invention in treated equines at 0, 7, 14, 21, 28, 35, 49, 63 and 70 days post-treatment. January-March, La Molina - Peru, 2007.

| Classification of the eggs | Control Before Tx | Treatment Number of eggs per animal (% efficacy) Oral endoparasiticidal gel Post-treatment (days) | | | | | | | | |
|---|---|---|---|---|---|---|---|---|---|---|
| | | 7 | 14 | 21 | 28 | 35 | 42 | 49 | 63 | 70 |
| *Strongylus* type eggs | EPG 595 | % 0 (100) | % 0 (100) | % 0 (100) | % 0 (100) | % 0 (100) | % 0 (100) | % 0 (100) | % 0 (100) | % 50 (91.6) |

The invention claimed is:

1. A bioadhesive endoparasiticidal gel composition comprising:
   a. from about 0.5% to about 5% weight/volume of doramectin;
   b. from about 1% to about 10% weight/volume of an organic solvent;
   c. from about 10% to about 60% weight/volume of polyvinylpyrrolidone;
   d. from about 25% to about 95% weight/volume of a diluent;
   e. from about 0.1% to about 5% weight/volume of a sweetening agent;
   f. from about 0.1% to about 4% weight/volume of a flavoring agent;
   h. from about 0.1% to about 1% weight/volume of a preservative; and
   i. from about 0.001% to about 0.01% weight/volume of a coloring agent.

2. The composition of claim 1, wherein the doramectin is present at a range of about 1.5% to about 2.5% weight/volume.

3. The composition of claim 1, wherein the organic solvent is present at a range of about 2.5% to about 3.5% weight/volume.

4. The composition of claim 1, wherein the organic solvent comprises one or more of N-methyl-2-pyrrolidone, 2-pyrrolidone, benzyl alcohol, glycerol formal, and mixtures thereof.

5. The composition of claim 1, wherein polyvinylpyrrolidone is present at a range of about 35% to about 45% weight/volume.

6. The composition of claim 1, wherein the diluent comprises one or more of propylene glycol, polyethylene glycol 300, polyethylene glycol 400, glycerin, polyethoxylated castor oil, macrogol 15 hydroxystearate, and mixtures thereof.

7. The composition of claim 1, wherein the sweetening agent is present at a range of about 0.5% to about 1.5% weight/volume.

8. The composition of claim 1, wherein the sweetening agent comprises one or more of sodium sucralose, sodium saccharin, sucrose, and mixtures thereof.

9. The composition of claim 1, wherein the flavoring agent is present at a range of about 1.5% to about 2.5% weight/volume.

10. The composition of claim 1, wherein the flavoring agent comprises one or more of a natural or synthetic essence of fruit.

11. The composition of claim 1, wherein the preservative is present at a range of about 0.18% to about 0.22% weight/volume.

12. The composition of claim 1, wherein the preservative comprises one or more of methylparaben, propylparaben, butylparaben, and mixtures thereof.

13. The composition of claim 1, wherein the coloring agent is present at a range of about 0.0015% to about 0.0025%.

14. The composition of claim 1, wherein the coloring agent comprises a water-soluble azo dye.

15. A method of treating a mammal suffering from a parasitic condition, comprising applying an endoparasiticidal gel comprising doramectin to the oral cavity of the mammal, the endoparasiticidal gel comprising:
   a. from about 0.5% to about 5% weight/volume of doramectin;

b. from about 1% to about 10% weight/volume of an organic solvent;
c. from about 10% to about 60% weight/volume of polyvinylpyrrolidone;
d. from about 25% to about 95% weight/volume of a diluent;
e. from about 0.1% to about 5% weight/volume of a sweetening agent;
f. from about 0.1% to about 4% weight/volume of a flavoring agent;
h. from about 0.1% to about 1% weight/volume of a preservative; and
i. from about 0.001% to about 0.01% weight/volume of a coloring agent.

16. The method of claim 15, wherein the mammal is an equidae.

17. The method of claim 15, wherein doramectin is administered to the mammal in an amount of about 200 µg per kg of body weight.

18. The method of claim 15, wherein the endoparasiticidal gel is applied in an amount of about 1 mL per 100 kg of body weight.

19. A method for preparing an oral endoparasiticidal gel composition comprising:
   a. mixing doramectin, a preservative, a coloring agent and an organic solvent until forming a solution "A",
   b. mixing a diluent with a sweetening agent until forming a solution "B",
   c. mixing solution "B" with polyvinylpyrrolidone until forming a gel "C",
   d. mixing gel "C" with solution "A" until forming a gel "D",
   e. mixing a flavoring agent with gel "D" until forming a gel "E".

20. The method of claim 19, further comprising the step of mixing gel "E" in a vacuum to form an air-free endoparasiticidal gel composition.

21. The method of claim 19, wherein the preservative comprises one or more of methylparaben, propylparaben, butylparaben, and mixtures thereof.

22. The method of claim 19, wherein the coloring agent comprises a water-soluble azo dye.

23. The method of claim 19, wherein the organic solvent comprises one or more of N-methyl-2-pyrrolidone, 2-pyrrolidone, benzyl alcohol, glycerol formal, and mixtures thereof.

24. The method of claim 19, wherein the diluent comprises one or more of propylene glycol, polyethylene glycol 300, polyethylene glycol 400, glycerin, polyethoxylated castor oil, macrogol 15 hydroxystearate, and mixtures thereof.

25. The method of claim 19, wherein the sweetening agent comprises one or more of sodium sucralose, sodium saccharin, sucrose, and mixtures thereof.

26. The method of claim 19, wherein the flavoring agent comprises one or more of a natural or synthetic essence of fruit.

* * * * *